(12) United States Patent
Skillrud et al.

(10) Patent No.: US 10,575,864 B2
(45) Date of Patent: Mar. 3, 2020

(54) SECURING ELEMENT FOR RESHEATHING AN INTRAVASCULAR DEVICE AND ASSOCIATED SYSTEMS AND METHODS

(71) Applicant: Covidien LP, Mansfield, MA (US)

(72) Inventors: Erik Skillrud, Newport Beach, CA (US); Daniel Deen, Signal Hill, CA (US); Evan Epstein, Costa Mesa, CA (US)

(73) Assignee: COVIDIEN LP, Mansfield, MA (US)

( * ) Notice: Subject to any disclaimer, the term of this patent is extended or adjusted under 35 U.S.C. 154(b) by 212 days.

(21) Appl. No.: 15/629,786

(22) Filed: Jun. 22, 2017

(65) Prior Publication Data

US 2018/0368863 A1 Dec. 27, 2018

(51) Int. Cl.
| | |
|---|---|
| *A61B 17/221* | (2006.01) |
| *A61B 17/22* | (2006.01) |
| *A61B 17/00* | (2006.01) |
| *A61B 90/00* | (2016.01) |
| *A61B 17/34* | (2006.01) |

(52) U.S. Cl.
CPC .. *A61B 17/221* (2013.01); *A61B 2017/00477* (2013.01); *A61B 2017/00862* (2013.01); *A61B 2017/2215* (2013.01); *A61B 2017/22034* (2013.01); *A61B 2017/22038* (2013.01); *A61B 2017/22044* (2013.01); *A61B 2017/3435* (2013.01); *A61B 2090/3966* (2016.02)

(58) Field of Classification Search
CPC .......... A61B 17/221; A61B 2017/2212; A61B 2017/2215; A61B 2017/3435
See application file for complete search history.

(56) References Cited

U.S. PATENT DOCUMENTS

| | | |
|---|---|---|
| 2,918,919 A | 12/1959 | Wallace |
| 2,943,626 A | 7/1960 | Dormia |
| 3,996,938 A | 12/1976 | Clark, III |
| 4,347,846 A | 9/1982 | Dormia |
| 4,611,594 A | 9/1986 | Grayhack et al. |
| 4,650,466 A | 3/1987 | Luther |
| 4,657,020 A | 4/1987 | Lifton |
| 4,699,147 A | 10/1987 | Chilson et al. |
| 4,790,812 A | 12/1988 | Hawkins, Jr. et al. |

(Continued)

FOREIGN PATENT DOCUMENTS

| | | |
|---|---|---|
| CN | 1640505 A | 7/2005 |
| CN | 102036611 A | 4/2011 |

(Continued)

*Primary Examiner* — Tuan V Nguyen

(74) *Attorney, Agent, or Firm* — Fortem IP LLP; Vijay Kumar

(57) ABSTRACT

Devices and methods for securing a cover of a retrieval device while the retrieval device is resheathed to a more proximal position within a delivery sheath are disclosed herein. A retrieval device may include, for example, a securing element configured to grip the cover when the retrieval device is pulled proximally, to thereby secure the cover. A method of positioning the retrieval device may include, for example: (a) advancing the retrieval device distally through a delivery sheath to a partially deployed state while the securing element is in a first state, and (b) retracting the clot retrieval proximally from the partially deployed state while the securing element is in a second state that grips the cover to secure the cover.

44 Claims, 8 Drawing Sheets

(56) References Cited

U.S. PATENT DOCUMENTS

| | | |
|---|---|---|
| 4,807,626 A | 2/1989 | McGirr |
| 4,832,055 A | 5/1989 | Palestrant |
| 4,873,978 A | 10/1989 | Ginsburg |
| 4,969,891 A | 11/1990 | Gewertz |
| 4,998,539 A | 3/1991 | Delsanti |
| 5,034,001 A | 7/1991 | Garrison et al. |
| 5,057,114 A | 10/1991 | Wittich et al. |
| 5,059,178 A | 10/1991 | Ya |
| 5,102,415 A | 4/1992 | Guenther et al. |
| 5,147,400 A | 9/1992 | Kaplan et al. |
| 5,152,777 A | 10/1992 | Goldberg et al. |
| 5,192,286 A | 3/1993 | Phan et al. |
| 5,300,086 A | 4/1994 | Gory et al. |
| 5,329,942 A | 7/1994 | Gunther et al. |
| 5,443,478 A | 8/1995 | Purdy |
| 5,449,372 A | 9/1995 | Schmaltz et al. |
| 5,458,375 A | 10/1995 | Anspach, Jr. et al. |
| 5,490,859 A | 2/1996 | Mische et al. |
| 5,496,330 A | 3/1996 | Bates et al. |
| 5,509,900 A | 4/1996 | Kirkman |
| 5,653,684 A | 8/1997 | Laptewicz et al. |
| 5,658,296 A | 8/1997 | Bates et al. |
| 5,709,704 A | 1/1998 | Nott et al. |
| 5,733,302 A | 3/1998 | Myler et al. |
| 5,741,325 A | 4/1998 | Chaikof et al. |
| 5,792,156 A | 8/1998 | Perouse |
| 5,827,324 A | 10/1998 | Cassell et al. |
| 5,846,251 A | 12/1998 | Hart |
| 5,895,398 A | 4/1999 | Wensel et al. |
| 5,941,869 A | 8/1999 | Patterson et al. |
| 5,947,995 A | 9/1999 | Samuels |
| 5,968,090 A | 10/1999 | Ratcliff et al. |
| 5,971,938 A | 10/1999 | Hart et al. |
| 5,972,019 A | 10/1999 | Engelson et al. |
| 5,984,957 A | 11/1999 | Laptewicz, Jr. et al. |
| 6,001,118 A | 12/1999 | Daniel et al. |
| 6,033,394 A | 3/2000 | Vidlund et al. |
| 6,042,598 A | 3/2000 | Tsugita et al. |
| 6,053,932 A | 4/2000 | Daniel et al. |
| 6,066,149 A | 5/2000 | Samson et al. |
| 6,066,158 A | 5/2000 | Engelson et al. |
| 6,096,053 A | 8/2000 | Bates |
| 6,099,534 A | 8/2000 | Bates et al. |
| 6,146,403 A | 11/2000 | St. Germain |
| 6,159,220 A | 12/2000 | Gobron et al. |
| 6,165,200 A | 12/2000 | Tsugita et al. |
| 6,168,603 B1 | 1/2001 | Leslie et al. |
| 6,174,318 B1 | 1/2001 | Bates et al. |
| 6,176,873 B1 | 1/2001 | Ouchi |
| 6,190,394 B1 | 2/2001 | Lind et al. |
| 6,217,609 B1 | 4/2001 | Haverkost |
| 6,221,006 B1 | 4/2001 | Dubrul et al. |
| 6,245,088 B1 | 6/2001 | Lowery |
| 6,245,089 B1 | 6/2001 | Daniel et al. |
| 6,248,113 B1 | 6/2001 | Fina |
| 6,264,664 B1 | 7/2001 | Avellanet |
| 6,302,895 B1 | 10/2001 | Gobron et al. |
| 6,309,399 B1 | 10/2001 | Barbut et al. |
| 6,348,056 B1 | 2/2002 | Bates et al. |
| 6,350,266 B1 | 2/2002 | White et al. |
| 6,364,895 B1 | 4/2002 | Greenhalgh |
| 6,371,971 B1 | 4/2002 | Tsugita et al. |
| 6,383,195 B1 | 5/2002 | Richard |
| 6,383,196 B1 | 5/2002 | Leslie et al. |
| 6,391,044 B1 | 5/2002 | Yadav et al. |
| 6,402,771 B1 | 6/2002 | Palmer et al. |
| 6,409,750 B1 | 6/2002 | Hyodoh et al. |
| 6,416,505 B1 | 7/2002 | Fleischman et al. |
| 6,425,909 B1 | 7/2002 | Dieck et al. |
| 6,436,112 B2 | 8/2002 | Wensel et al. |
| 6,443,972 B1 | 9/2002 | Bosma et al. |
| 6,458,139 B1 | 10/2002 | Palmer et al. |
| 6,485,497 B2 | 11/2002 | Wensel et al. |
| 6,494,884 B2 | 12/2002 | Gifford, III et al. |
| 6,506,204 B2 | 1/2003 | Mazzocchi |
| 6,514,273 B1 | 2/2003 | Voss et al. |
| 6,530,935 B2 | 3/2003 | Wensel et al. |
| 6,540,657 B2 | 4/2003 | Cross, III et al. |
| 6,540,768 B1 | 4/2003 | Diaz et al. |
| 6,551,342 B1 | 4/2003 | Shen et al. |
| 6,575,997 B1 | 6/2003 | Palmer et al. |
| 6,585,753 B2 | 7/2003 | Eder et al. |
| 6,592,605 B2 | 7/2003 | Lenker et al. |
| 6,592,607 B1 | 7/2003 | Palmer et al. |
| 6,602,271 B2 | 8/2003 | Adams et al. |
| 6,605,102 B1 | 8/2003 | Mazzocchi et al. |
| 6,610,077 B1 | 8/2003 | Hancock et al. |
| 6,616,679 B1 | 9/2003 | Khosravi et al. |
| 6,620,148 B1 | 9/2003 | Tsugita |
| 6,635,068 B1 | 10/2003 | Dubrul et al. |
| 6,636,758 B2 | 10/2003 | Sanchez et al. |
| 6,638,245 B2 | 10/2003 | Miller et al. |
| 6,638,293 B1 | 10/2003 | Makower et al. |
| 6,641,590 B1 | 11/2003 | Palmer et al. |
| 6,645,199 B1 | 11/2003 | Jenkins et al. |
| 6,652,505 B1 | 11/2003 | Tsugita |
| 6,652,548 B2 | 11/2003 | Evans et al. |
| 6,660,021 B1 | 12/2003 | Palmer et al. |
| 6,663,650 B2 | 12/2003 | Sepetka et al. |
| 6,673,042 B1 | 1/2004 | Samson et al. |
| 6,679,893 B1 | 1/2004 | Tran |
| 6,685,738 B2 | 2/2004 | Chouinard et al. |
| 6,692,508 B2 | 2/2004 | Wensel et al. |
| 6,692,509 B2 | 2/2004 | Wensel et al. |
| 6,695,858 B2 | 2/2004 | Dubrul et al. |
| 6,702,782 B2 | 3/2004 | Miller et al. |
| 6,730,104 B1 | 5/2004 | Sepetka et al. |
| 6,745,080 B2 | 6/2004 | Koblish |
| 6,746,468 B1 | 6/2004 | Sepetka et al. |
| 6,749,619 B2 | 6/2004 | Ouriel et al. |
| 6,755,813 B2 | 6/2004 | Ouriel et al. |
| 6,800,080 B1 | 10/2004 | Bates |
| 6,824,545 B2 | 11/2004 | Sepetka et al. |
| 6,855,155 B2 | 2/2005 | Denardo et al. |
| 6,872,211 B2 | 3/2005 | White et al. |
| 6,872,216 B2 | 3/2005 | Daniel et al. |
| 6,890,341 B2 | 5/2005 | Dieck et al. |
| 6,893,431 B2 | 5/2005 | Naimark et al. |
| 6,905,503 B2 | 6/2005 | Gifford, III et al. |
| 6,913,612 B2 | 7/2005 | Palmer et al. |
| 6,936,059 B2 | 8/2005 | Belef |
| 6,939,362 B2 | 9/2005 | Boyle et al. |
| 6,945,977 B2 | 9/2005 | Demarais et al. |
| 6,953,465 B2 | 10/2005 | Dieck et al. |
| 6,964,672 B2 | 11/2005 | Brady et al. |
| 7,004,955 B2 | 2/2006 | Shen et al. |
| 7,004,956 B2 | 2/2006 | Palmer et al. |
| 7,037,320 B2 | 5/2006 | Brady et al. |
| 7,041,126 B2 | 5/2006 | Shin et al. |
| 7,048,014 B2 | 5/2006 | Hyodoh et al. |
| 7,058,456 B2 | 6/2006 | Pierce |
| 7,097,653 B2 | 8/2006 | Freudenthal et al. |
| 7,101,380 B2 | 9/2006 | Khachin et al. |
| 7,169,165 B2 | 1/2007 | Belef et al. |
| 7,179,273 B1 | 2/2007 | Palmer et al. |
| 7,182,771 B1 | 2/2007 | Houser et al. |
| 7,235,061 B2 | 6/2007 | Tsugita |
| 7,240,516 B2 | 7/2007 | Pryor |
| 7,399,308 B2 | 7/2008 | Borillo et al. |
| 7,534,252 B2 | 5/2009 | Sepetka et al. |
| 7,578,830 B2 | 8/2009 | Kusleika et al. |
| 7,621,870 B2 | 11/2009 | Berrada et al. |
| 7,837,702 B2 | 11/2010 | Bates |
| 8,070,791 B2 | 12/2011 | Ferrera et al. |
| 8,088,140 B2 | 1/2012 | Ferrera et al. |
| 8,105,333 B2 | 1/2012 | Sepetka et al. |
| 8,197,493 B2 | 6/2012 | Ferrera et al. |
| 8,603,014 B2 | 12/2013 | Alleman et al. |
| 8,837,800 B1 | 9/2014 | Bammer et al. |
| 9,119,656 B2 | 9/2015 | Bose et al. |
| 9,126,018 B1 | 9/2015 | Garrison |
| 9,211,132 B2 | 12/2015 | Bowman |
| 9,241,699 B1 | 1/2016 | Kume et al. |
| 9,265,512 B2 | 2/2016 | Garrison et al. |

(56) References Cited

U.S. PATENT DOCUMENTS

| | | |
|---|---|---|
| 9,308,007 B2 | 4/2016 | Cully et al. |
| 9,399,118 B2 | 7/2016 | Kume et al. |
| 9,445,828 B2 | 9/2016 | Turjman et al. |
| 9,445,829 B2 | 9/2016 | Brady et al. |
| 9,492,637 B2 | 11/2016 | Garrison et al. |
| 9,539,022 B2 | 1/2017 | Bowman |
| 9,561,345 B2 | 2/2017 | Garrison et al. |
| 9,579,119 B2 | 2/2017 | Cully et al. |
| 9,585,741 B2 | 3/2017 | Ma |
| 9,642,635 B2 | 5/2017 | Vale et al. |
| 9,655,633 B2 | 5/2017 | Leynov et al. |
| 9,737,318 B2 | 8/2017 | Monstadt et al. |
| 9,770,251 B2 | 9/2017 | Bowman et al. |
| 9,801,643 B2 | 10/2017 | Hansen et al. |
| 9,861,783 B2 | 1/2018 | Garrison et al. |
| 9,993,257 B2 | 6/2018 | Losordo et al. |
| 10,028,782 B2 | 7/2018 | Orion |
| 10,029,008 B2 | 7/2018 | Creighton |
| 10,039,906 B2 | 8/2018 | Kume et al. |
| 2001/0041909 A1 | 11/2001 | Tsugita et al. |
| 2001/0044632 A1 | 11/2001 | Daniel et al. |
| 2001/0044634 A1 | 11/2001 | Don Michael et al. |
| 2001/0051810 A1 | 12/2001 | Dubrul et al. |
| 2002/0002396 A1 | 1/2002 | Fulkerson |
| 2002/0004667 A1 | 1/2002 | Adams et al. |
| 2002/0026211 A1 | 2/2002 | Khosravi et al. |
| 2002/0058904 A1 | 5/2002 | Boock et al. |
| 2002/0062135 A1 | 5/2002 | Mazzocchi et al. |
| 2002/0072764 A1 | 6/2002 | Sepetka et al. |
| 2002/0082558 A1 | 6/2002 | Samson et al. |
| 2002/0123765 A1 | 9/2002 | Sepetka et al. |
| 2002/0138094 A1 | 9/2002 | Borillo et al. |
| 2002/0151928 A1 | 10/2002 | Leslie et al. |
| 2002/0169474 A1 | 11/2002 | Kusleika et al. |
| 2002/0188314 A1 | 12/2002 | Anderson et al. |
| 2002/0193825 A1 | 12/2002 | McGuckin et al. |
| 2003/0004542 A1 | 1/2003 | Wensel et al. |
| 2003/0023265 A1 | 1/2003 | Forber |
| 2003/0040771 A1 | 2/2003 | Hyodoh et al. |
| 2003/0050663 A1 | 3/2003 | Khachin et al. |
| 2003/0060782 A1 | 3/2003 | Bose et al. |
| 2003/0093087 A1 | 5/2003 | Jones et al. |
| 2003/0144687 A1 | 7/2003 | Brady et al. |
| 2003/0153935 A1 | 8/2003 | Mialhe |
| 2003/0176884 A1 | 9/2003 | Berrada et al. |
| 2003/0195556 A1 | 10/2003 | Stack et al. |
| 2004/0068288 A1 | 4/2004 | Palmer et al. |
| 2004/0073243 A1 | 4/2004 | Sepetka et al. |
| 2004/0079429 A1 | 4/2004 | Miller et al. |
| 2004/0133232 A1 | 7/2004 | Rosenbluth et al. |
| 2004/0138692 A1 | 7/2004 | Phung et al. |
| 2004/0153025 A1 | 8/2004 | Seifert et al. |
| 2004/0153118 A1 | 8/2004 | Clubb et al. |
| 2004/0172056 A1 | 9/2004 | Guterman et al. |
| 2004/0199201 A1 | 10/2004 | Kellett et al. |
| 2004/0199243 A1 | 10/2004 | Yodfat |
| 2004/0210116 A1 | 10/2004 | Nakao |
| 2004/0267301 A1 | 12/2004 | Boylan et al. |
| 2005/0004594 A1 | 1/2005 | Nool et al. |
| 2005/0033348 A1 | 2/2005 | Sepetka et al. |
| 2005/0038447 A1 | 2/2005 | Huffmaster |
| 2005/0043680 A1 | 2/2005 | Segal et al. |
| 2005/0043756 A1 | 2/2005 | Lavelle et al. |
| 2005/0049619 A1 | 3/2005 | Sepetka et al. |
| 2005/0055033 A1 | 3/2005 | Leslie et al. |
| 2005/0055047 A1 | 3/2005 | Greenhalgh |
| 2005/0059995 A1 | 3/2005 | Sepetka et al. |
| 2005/0080356 A1 | 4/2005 | Dapolito et al. |
| 2005/0085826 A1 | 4/2005 | Nair et al. |
| 2005/0085847 A1 | 4/2005 | Galdonik et al. |
| 2005/0085849 A1 | 4/2005 | Sepetka et al. |
| 2005/0090857 A1 | 4/2005 | Kusleika et al. |
| 2005/0090858 A1 | 4/2005 | Pavlovic |
| 2005/0125024 A1 | 6/2005 | Sepetka et al. |
| 2005/0131450 A1 | 6/2005 | Nicholson et al. |
| 2005/0171566 A1 | 8/2005 | Kanamaru |
| 2005/0203571 A1 | 9/2005 | Mazzocchi et al. |
| 2005/0209609 A1 | 9/2005 | Wallace |
| 2005/0216030 A1 | 9/2005 | Sepetka et al. |
| 2005/0216050 A1 | 9/2005 | Sepetka et al. |
| 2005/0234501 A1 | 10/2005 | Barone |
| 2005/0234505 A1 | 10/2005 | Diaz et al. |
| 2005/0277978 A1 | 12/2005 | Greenhalgh |
| 2005/0283166 A1 | 12/2005 | Greenhalgh |
| 2005/0283186 A1 | 12/2005 | Berrada et al. |
| 2006/0004404 A1 | 1/2006 | Khachin et al. |
| 2006/0009784 A1 | 1/2006 | Behl et al. |
| 2006/0030925 A1 | 2/2006 | Pryor |
| 2006/0047286 A1 | 3/2006 | West |
| 2006/0058836 A1 | 3/2006 | Bose et al. |
| 2006/0058837 A1 | 3/2006 | Bose et al. |
| 2006/0058838 A1 | 3/2006 | Bose et al. |
| 2006/0095070 A1 | 5/2006 | Gilson et al. |
| 2006/0129166 A1 | 6/2006 | Lavelle |
| 2006/0129180 A1 | 6/2006 | Tsugita et al. |
| 2006/0155305 A1 | 7/2006 | Freudenthal et al. |
| 2006/0190070 A1 | 8/2006 | Dieck et al. |
| 2006/0195137 A1 | 8/2006 | Sepetka et al. |
| 2006/0229638 A1 | 10/2006 | Abrams et al. |
| 2006/0253145 A1 | 11/2006 | Lucas |
| 2006/0271153 A1 | 11/2006 | Garcia et al. |
| 2006/0276805 A1 | 12/2006 | Yu |
| 2006/0282111 A1 | 12/2006 | Morsi |
| 2006/0287668 A1 | 12/2006 | Fawzi et al. |
| 2007/0112374 A1 | 5/2007 | Paul et al. |
| 2007/0118165 A1 | 5/2007 | DeMello et al. |
| 2007/0149996 A1 | 6/2007 | Coughlin |
| 2007/0185500 A1 | 8/2007 | Martin et al. |
| 2007/0185501 A1 | 8/2007 | Martin et al. |
| 2007/0197103 A1 | 8/2007 | Martin et al. |
| 2007/0198029 A1 | 8/2007 | Martin et al. |
| 2007/0198030 A1 | 8/2007 | Martin et al. |
| 2007/0198051 A1 | 8/2007 | Clubb et al. |
| 2007/0225749 A1 | 9/2007 | Martin et al. |
| 2007/0233236 A1 | 10/2007 | Pryor |
| 2007/0265656 A1 | 11/2007 | Amplatz et al. |
| 2008/0109031 A1 | 5/2008 | Sepetka et al. |
| 2008/0183198 A1 | 7/2008 | Sepetka et al. |
| 2008/0188885 A1 | 8/2008 | Sepetka et al. |
| 2008/0262528 A1 | 10/2008 | Martin |
| 2008/0262532 A1 | 10/2008 | Martin |
| 2009/0069828 A1 | 3/2009 | Martin et al. |
| 2009/0105722 A1 | 4/2009 | Fulkerson et al. |
| 2009/0105737 A1 | 4/2009 | Fulkerson et al. |
| 2009/0125053 A1 | 5/2009 | Ferrera et al. |
| 2009/0192518 A1 | 7/2009 | Golden et al. |
| 2009/0287291 A1 | 11/2009 | Becking et al. |
| 2009/0299393 A1 | 12/2009 | Martin et al. |
| 2010/0076452 A1 | 3/2010 | Sepetka et al. |
| 2010/0100106 A1 | 4/2010 | Ferrera |
| 2010/0174309 A1 | 7/2010 | Fulkerson et al. |
| 2010/0185210 A1 | 7/2010 | Hauser et al. |
| 2010/0217187 A1 | 8/2010 | Fulkerson et al. |
| 2010/0256600 A1 | 10/2010 | Ferrera |
| 2010/0318097 A1 | 12/2010 | Ferrera et al. |
| 2011/0160742 A1 | 6/2011 | Ferrera et al. |
| 2011/0160757 A1 | 6/2011 | Ferrera et al. |
| 2011/0160760 A1 | 6/2011 | Ferrera et al. |
| 2011/0160761 A1 | 6/2011 | Ferrera et al. |
| 2011/0160763 A1 | 6/2011 | Ferrera et al. |
| 2011/0166586 A1 | 7/2011 | Sepetka et al. |
| 2011/0288572 A1 | 11/2011 | Martin |
| 2011/0319917 A1 | 12/2011 | Ferrera et al. |
| 2012/0143230 A1 | 6/2012 | Sepetka et al. |
| 2012/0197285 A1 | 8/2012 | Martin et al. |
| 2013/0030461 A1 | 1/2013 | Marks et al. |
| 2013/0281788 A1 | 10/2013 | Garrison |
| 2014/0276074 A1 | 9/2014 | Warner |
| 2014/0276403 A1* | 9/2014 | Follmer ............ A61B 17/22032 604/103.02 |
| 2014/0317589 A1* | 10/2014 | Bowman, Jr. ............ G06F 17/50 716/139 |
| 2014/0343595 A1 | 11/2014 | Monstadt et al. |
| 2015/0359547 A1 | 12/2015 | Vale et al. |

(56) References Cited

U.S. PATENT DOCUMENTS

| | | |
|---|---|---|
| 2016/0015402 A1 | 1/2016 | Brady et al. |
| 2016/0015935 A1 | 1/2016 | Chan et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113665 A1 | 4/2016 | Brady et al. |
| 2016/0151618 A1 | 6/2016 | Powers et al. |
| 2016/0157985 A1 | 6/2016 | Vo et al. |
| 2016/0199620 A1 | 7/2016 | Pokorney et al. |
| 2016/0296690 A1 | 10/2016 | Kume et al. |
| 2016/0302808 A1 | 10/2016 | Loganathan et al. |
| 2016/0354098 A1 | 12/2016 | Martin et al. |
| 2016/0375180 A1 | 12/2016 | Anzai |
| 2017/0079766 A1 | 3/2017 | Wang et al. |
| 2017/0079767 A1 | 3/2017 | Leon-Yip |
| 2017/0086862 A1 | 3/2017 | Vale et al. |
| 2017/0100143 A1 | 4/2017 | Grandfield |
| 2017/0105743 A1 | 4/2017 | Vale et al. |
| 2017/0164963 A1 | 6/2017 | Goyal |
| 2017/0215902 A1 | 8/2017 | Leynov et al. |
| 2017/0224953 A1 | 8/2017 | Tran et al. |
| 2017/0281909 A1 | 10/2017 | Northrop et al. |
| 2017/0290599 A1 | 10/2017 | Youn et al. |
| 2018/0049762 A1 | 2/2018 | Seip et al. |
| 2018/0084982 A1 | 3/2018 | Yamashita et al. |
| 2018/0116717 A1 | 5/2018 | Taff et al. |
| 2018/0132876 A1 | 5/2018 | Zaidat |
| 2018/0140314 A1 | 5/2018 | Goyal et al. |
| 2018/0140315 A1 | 5/2018 | Bowman et al. |
| 2018/0140354 A1 | 5/2018 | Lam et al. |
| 2018/0185614 A1 | 7/2018 | Garrison et al. |

FOREIGN PATENT DOCUMENTS

| | | |
|---|---|---|
| DE | 3501707 A1 | 7/1986 |
| EP | 200668 A2 | 11/1986 |
| EP | 1312314 A1 | 5/2003 |
| EP | 2319575 B1 | 11/2013 |
| JP | 2002537943 A | 11/2002 |
| JP | 2007-522881 A | 8/2007 |
| JP | 2007252951 A | 10/2007 |
| JP | 2008539958 A | 11/2008 |
| JP | 2011508635 | 3/2011 |
| JP | 2014004219 A | 1/2014 |
| JP | 2018118132 A | 8/2018 |
| KR | 20180102877 A | 9/2018 |
| WO | WO-9601591 A1 | 1/1986 |
| WO | WO-94/09845 A1 | 5/1994 |
| WO | WO-95/09586 A1 | 4/1995 |
| WO | WO-96/17634 A2 | 6/1996 |
| WO | WO-96/19941-1 | 7/1996 |
| WO | WO-97/27808 A1 | 8/1997 |
| WO | WO-97/27893 A1 | 8/1997 |
| WO | WO-98/03120 A1 | 1/1998 |
| WO | WO-00/53120 A1 | 9/2000 |
| WO | WO-0072909 A1 | 12/2000 |
| WO | WO-01/32254 A1 | 5/2001 |
| WO | WO-01/54622 A1 | 8/2001 |
| WO | WO-01/67967 A1 | 9/2001 |
| WO | WO-02/02162 | 1/2002 |
| WO | WO-02/28291 A2 | 4/2002 |
| WO | WO-03/000334 A1 | 1/2003 |
| WO | WO-03/061730 A2 | 7/2003 |
| WO | WO-03/089039 A1 | 10/2003 |
| WO | WO-2006/031410 A2 | 3/2006 |
| WO | WO-2006/122076 A1 | 11/2006 |
| WO | WO-2007092820 A2 | 8/2007 |
| WO | WO-2008/036156 A1 | 3/2008 |
| WO | WO-2008036156 | 3/2008 |
| WO | WO-2008/131116 A1 | 10/2008 |
| WO | WO-2009/034456 A2 | 3/2009 |
| WO | WO-2009/086482 A1 | 7/2009 |
| WO | WO-2011/091383 A1 | 7/2011 |
| WO | WO-2011091383 | 7/2011 |
| WO | WO-2012009675 A2 | 1/2012 |
| WO | WO-2012/162437 A1 | 11/2012 |
| WO | WO-2013/106146 A1 | 7/2013 |
| WO | 2015141317 A1 | 9/2015 |
| WO | 2017192999 A1 | 11/2017 |
| WO | 2018019829 A1 | 2/2018 |
| WO | 2018033401 A1 | 2/2018 |
| WO | 2018046408 A2 | 3/2018 |
| WO | 2018137029 A1 | 8/2018 |
| WO | 2018137030 A1 | 8/2018 |
| WO | 2018145212 A1 | 8/2018 |
| WO | 2018156813 A1 | 8/2018 |
| WO | 2018172891 A1 | 9/2018 |
| WO | 2018187776 A1 | 10/2018 |

\* cited by examiner

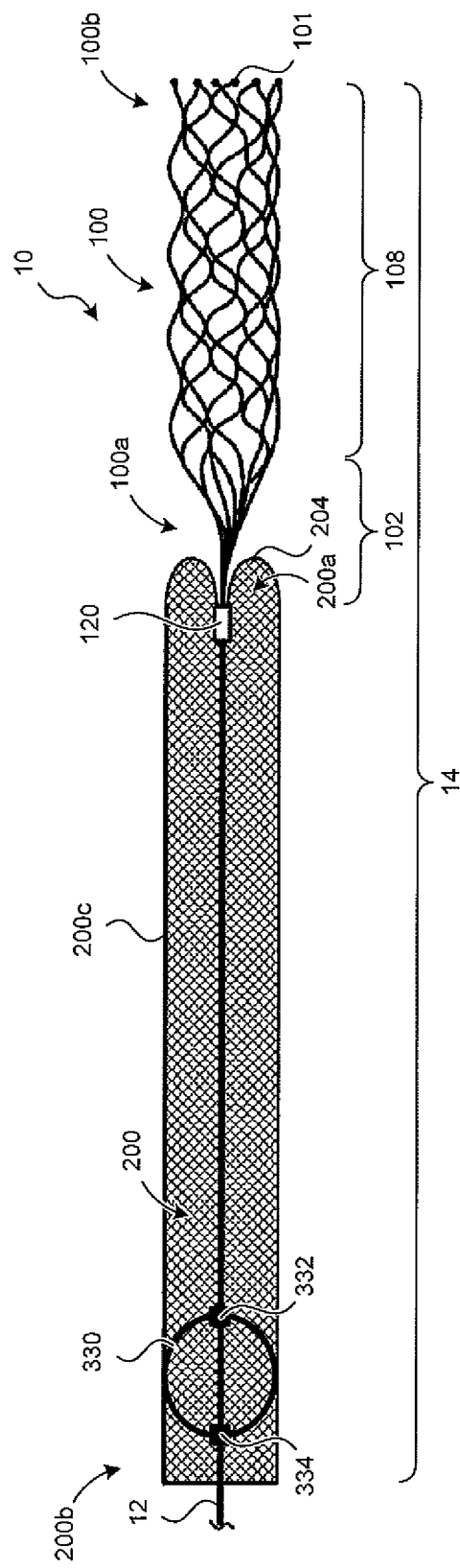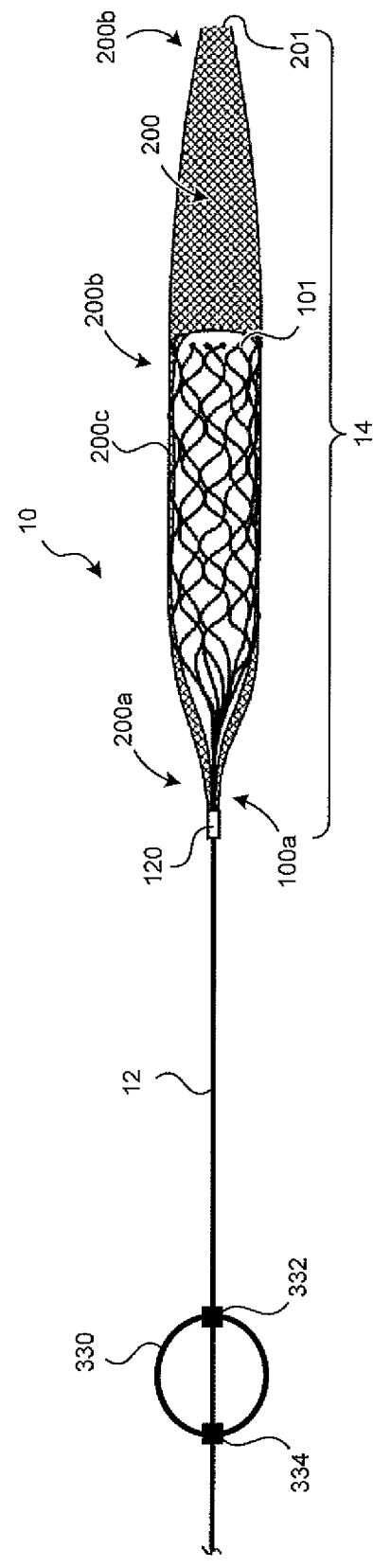
FIG. 1A
FIG. 1B

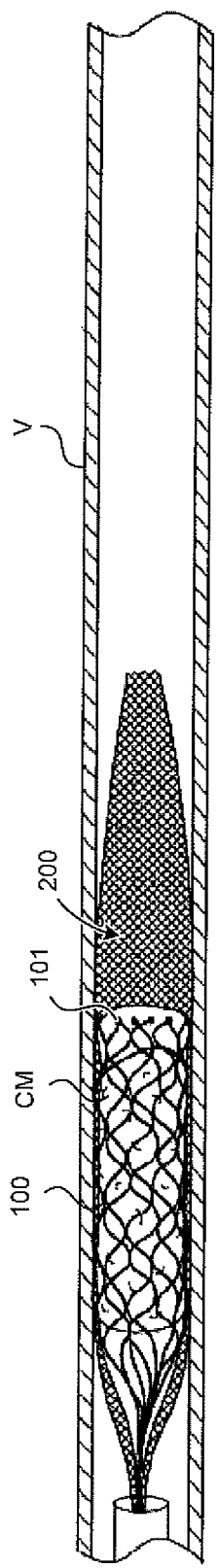

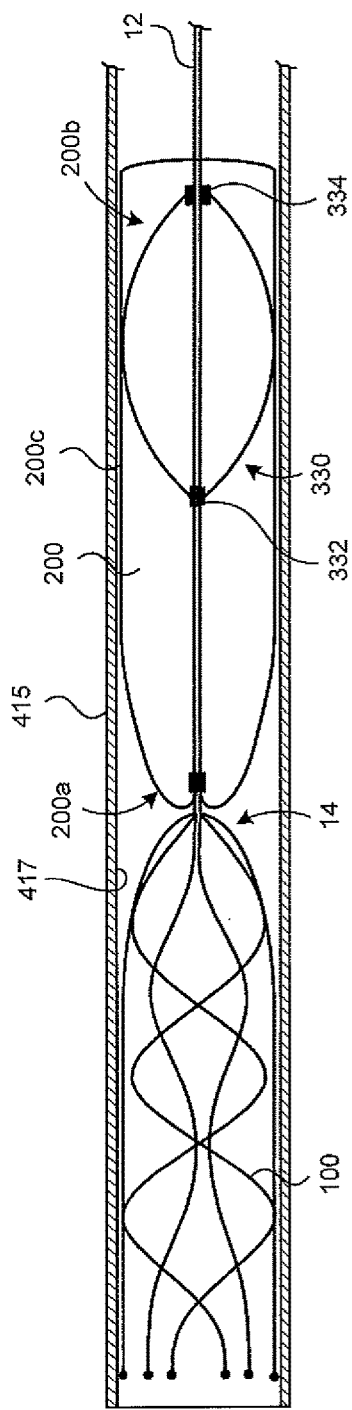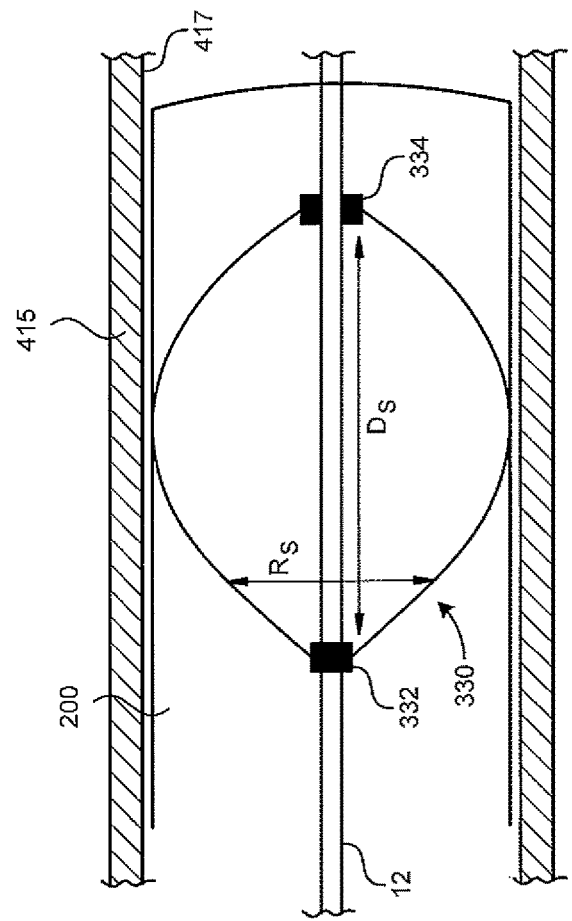
FIG. 3A
FIG. 3B

SECURING ELEMENT FOR RESHEATHING AN INTRAVASCULAR DEVICE AND ASSOCIATED SYSTEMS AND METHODS

TECHNICAL FIELD

The present technology relates generally to devices and methods for securing a cover of a retrieval device while the retrieval device is resheathed to a more proximal position within a delivery sheath.

BACKGROUND

Many medical procedures use medical device(s) to remove an obstruction (such as clot material) from a body lumen, vessel, or other organ. An inherent risk in such procedures is that mobilizing or otherwise disturbing the obstruction can potentially create further harm if the obstruction or a fragment thereof dislodges from the retrieval device. If all or a portion of the obstruction breaks free from the device and flows downstream, it is highly likely that the free material will become trapped in smaller and more tortuous anatomy. In many cases, the physician will no longer be able to use the same retrieval device to again remove the obstruction because the device may be too large and/or immobile to move the device to the site of the new obstruction.

Even in successful procedures, a physician must be cautious to prevent the walls of the vessel or body lumen from imparting undesired forces to shear or dislodge the obstruction as it passes through the vasculature during removal. These forces have the potential of fragmenting the obstruction. In some cases, the obstruction can simply break free from the retrieval device and can lodge in a new area causing more concern than the original blockage.

Procedures for treating ischemic stroke by restoring flow within the cerebral vasculature are subject to the above concerns. The brain relies on its arteries and veins to supply oxygenated blood from the heart and lungs and to remove carbon dioxide and cellular waste from brain tissue. Blockages that interfere with this blood supply eventually cause the brain tissue to stop functioning. If the disruption in blood occurs for a sufficient amount of time, the continued lack of nutrients and oxygen causes irreversible cell death (infarction). Accordingly, it is desirable to provide immediate medical treatment of an ischemic stroke. To access the cerebral vasculature, a physician typically advances a catheter from a remote part of the body (typically a leg) through the abdominal vasculature and into the cerebral region of the vasculature. Once within the cerebral vasculature, the physician deploys a device for retrieval of the obstruction causing the blockage. Concerns about dislodged obstructions or the migration of dislodged fragments increases the duration of the procedure at time when restoration of blood flow is paramount. Furthermore, a physician might be unaware of one or more fragments that dislodge from the initial obstruction and cause blockage of smaller more distal vessels.

Many physicians currently perform thrombectomies (i.e. clot removal) with stents to resolve ischemic stroke. Typically, the physician deploys a stent into the clot in an attempt to push the clot to the side of the vessel and re-establish blood flow. Tissue plasminogen activator ("tPA") is often injected into the bloodstream through an intravenous line to break down a clot. However, it takes time for the tPA to reach the clot because the tPA must travel through the vasculature and only begins to break up the clot once it reaches the clot material. tPA is also often administered to supplement the effectiveness of the stent. Yet, if attempts at clot dissolution are ineffective or incomplete, the physician can attempt to remove the stent while it is expanded against or enmeshed within the clot. In doing so, the physician must effectively drag the clot through the vasculature, in a proximal direction, into a guide catheter located within vessels in the patient's neck (typically the carotid artery). While this procedure has been shown to be effective in the clinic and is easy for the physician to perform, there remain some distinct disadvantages to using this approach.

For example, one disadvantage is that the stent may not sufficiently retain the clot as it pulls the clot to the catheter. In such a case, some or all of the clot might remain the vasculature. Another risk is that as the stent mobilizes the clot from the original blockage site, the clot might not adhere to the stent as the stent is withdrawn toward the catheter. This is a particular risk when passing through bifurcations and tortuous anatomy. Furthermore, blood flow can carry the clot (or fragments of the clot) into a branching vessel at a bifurcation. If the clot is successfully brought to the end of the guide catheter in the carotid artery, yet another risk is that the clot may be "stripped" or "sheared" from the stent as the stent enters the guide catheter. Regardless, simply dragging an expanded stent (either fully or partially expanded) can result in undesired trauma to the vessel. In most cases, since the stent is oversized compared to the vessel, dragging a fixed metallic (or other) structure can pull the arteries and/or strip the cellular lining from the vessel, causing further trauma such as a hemorrhagic stroke (leakage of blood from a cerebral vessel). Also, the stent can become lodged on plaque on the vessel walls resulting in further vascular damage.

In view of the above, there remains a need for improved devices and methods that can remove occlusions from body lumens and/or vessels.

SUMMARY

At least some of the embodiments disclosed herein are devices, systems, and methods for retrieving clot material from a blood vessel lumen. For example, some embodiments are directed to a retrieval device (such as a clot retrieving device) that includes an elongated shaft configured to be intravascularly positioned at or adjacent clot material within a blood vessel lumen, and a retrieval assembly coupled to a distal region of the elongated shaft. The retrieval assembly may include a flexible cover and a capture structure. The retrieval assembly may be deployed within the blood vessel lumen at or near the clot material such that the capture structure engages or otherwise becomes enmeshed with at least a portion of the clot material, and at least a portion of the cover presses outward against the blood vessel wall proximal of the capture structure. Pulling the elongated shaft proximally everts the cover over the capture structure such that the cover at least partially ensheathes the capture structure and associated clot material. The retrieval assembly can then be withdrawn to remove the retrieval device and associated clot material from the patient.

In at least some embodiments of the present technology, a securing element can be used to secure the cover while the retrieval device is at least partially resheathed within a delivery sheath and while the retrieval assembly is still in the vasculature. Some embodiments of the securing element are attached to the elongated shaft of the retrieval device and configured to exert a force against the cover when the retrieval device is pulled proximally to thereby secure the cover.

The subject technology is illustrated, for example, according to various aspects described below. Various examples of aspects of the subject technology are described as numbered clauses (1, 2, 3, etc.) for convenience. These are provided as examples and do not limit the subject technology. It is noted that any of the dependent clauses may be combined in any combination, and placed into a respective independent clause, e.g., clause 1, clause 13, or clause 17. The other clauses can be presented in a similar manner.

1. A retrieval device deployable through a delivery sheath, the device comprising:
   an elongated shaft;
   a retrieval structure coupled to a distal zone of the elongated shaft, the retrieval structure including a capture structure and a cover having (a) a first portion coupled to the distal zone of the elongated shaft at a location proximal of the capture structure and (b) a free second portion, wherein, in a delivery state, the second portion of the cover extends proximally from the first portion; and
   a securing element coupled to the elongated shaft proximal to the first portion of the cover,
   wherein, when the cover is in the delivery state and at least a portion of the cover and at least a portion of the securing element are positioned within the delivery sheath, moving the retrieval device proximally increases an outward force exerted by the securing element against at least a portion of the cover and an inner surface of the delivery sheath, thereby inhibiting movement of the second portion of the cover relative to the elongated shaft.

2. The retrieval device of clause 1 wherein the cover extends continuously between the first portion and the second portion, and wherein the securing element exerts the outward force against the cover nearer to the second portion than the first portion.

3. The retrieval device of clause 1 wherein:
   the securing element is in a first state when positioned at least partially within the delivery sheath and the retrieval device is moved proximally with respect to the delivery sheath,
   the securing element is in a second state when positioned at least partially within the delivery sheath and the retrieval device is moved distally with respect to the delivery sheath, and
   the securing element exerts an outward force against the cover that is less in the second state than in the first state.

4. The retrieval device of clause 1 wherein:
   the securing element is in a first state when positioned at least partially within the delivery sheath and the retrieval device is moved proximally with respect to the delivery sheath,
   the securing element is in a second state when positioned at least partially within the delivery sheath and the retrieval device is moved distally with respect to the delivery sheath, and
   the securing element has a cross-sectional area that is greater in the first state than in the second state.

5. The retrieval device of clause 1 wherein the securing element is a braid or stent coupled to the elongated shaft at a first connector and a second connector, and wherein the first connector is proximal to the second connector along the shaft.

6. The retrieval device of clause 5 wherein at least one of the first and second connectors is fixed to the elongated shaft.

7. The retrieval device of clause 5 wherein at least one of the first and second connectors is slidably coupled to the elongated shaft and the other of the first and second connectors is fixed to the elongated shaft.

8. The retrieval device of clause 5 wherein the securing element includes a plurality of struts extending from the first connector to the second connector.

9. The retrieval device of clause 1 wherein the securing element is at least one of a laser cut sphere, a compressible foam or polymer pad, and a braided structure.

10. The retrieval device of clause 1 wherein at least one of the capture structure and the cover is a mesh.

11. The retrieval device of clause 1 wherein the capture structure is a stent and the cover is a braid.

12. The retrieval device of clause 1 wherein, when the retrieval structure is in the delivery state and the securing element is outside of the delivery sheath and within a vessel lumen, the securing element is configured to expand outward against the cover within the vessel lumen.

13. A method of positioning a retrieval device, the method comprising:
    advancing at least a portion of a retrieval structure of a retrieval device distally from a delivery sheath to a partially deployed state, wherein the retrieval structure is coupled to an elongated shaft, and wherein (a) during advancement, a securing element coupled to the elongated shaft is in a first configuration and a cover of the retrieval structure extends proximally relative to a capture structure of the retrieval structure, and (b) in the partially deployed state, at least a distal portion of the capture structure is distal of the delivery sheath and at least a portion of the cover remains within the delivery sheath; and
    retracting the retrieval device proximally such that the securing element expands radially to a second configuration wherein the securing element exerts an outward force against the cover that is greater than when in the first configuration.

14. The method of clause 13 wherein:
    the cover has a first portion coupled to the elongated shaft, a free second portion, and extends continuously between the first portion and second portion, and
    in the second configuration, the securing element exerts the outward force against the cover nearer to the second portion than the first portion and the securing element is configured to prevent substantial movement of the second portion of the cover relative to the first portion of the cover.

15. The method of clause 13 wherein the securing element has a cross-sectional area that is greater in the second configuration than in the first configuration.

16. The method of clause 13 wherein the securing element does not exert a force against the cover in the first configuration.

17. A system for retrieving vascular material (such as clot), the system comprising:
    a delivery sheath having a distal portion;
    a retrieval device including an elongated shaft, a retrieval structure, and a securing element, wherein:
       the retrieval structure is coupled to a distal zone of the elongated shaft and includes a capture structure and a cover,
       the cover has a first portion coupled to the distal zone of the elongated shaft and a free second portion, in a partially deployed state, at least a distal portion of the capture structure extends past the distal portion of the delivery sheath, at least the second portion of the cover is within the delivery sheath, and the second portion of the cover extends proximally from the first portion, and the securing element is coupled to the elongated shaft proximal to the first portion of the cover, and the securing element is configured to expand when the device is retracted proximally from the partially deployed state such that the securing element grips at least a portion of the cover between the securing element and an inner surface of the delivery sheath, thereby preventing substantial movement of the second portion of the cover relative to the first portion of the cover while the retrieval device is retracted proximally.

18. The system of clause 17 wherein the capture structure is a stent and the cover is a braid.

19. The system of clause 17 wherein the securing element is coupled to the elongated shaft at a first connector and a second connector, wherein the first connector is proximal to the second connector along the shaft, and wherein the first connector is slidably coupled to the elongated shaft.

20. The system of clause 17 wherein the cover extends continuously between the first portion and the second portion, and wherein the securing element grips the cover nearer to the second portion than the first portion.

Additional features and advantages of the subject technology will be set forth in the description below, and in part will be apparent from the description, or may be learned by practice of the subject technology. The advantages of the subject technology will be realized and attained by the structure particularly pointed out in the written description and claims hereof as well as the appended drawings.

It is to be understood that both the foregoing general description and the following detailed description are explanatory and are intended to provide examples and further explanation of the subject technology as claimed.

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present disclosure.

FIG. 1A is a side view of a distal portion of a clot retrieval device shown with a retrieval assembly in a first configuration in accordance with the present technology.

FIG. 1B is a side view of the distal portion of the clot retrieval device of FIG. 1A, shown with the retrieval assembly shown in a second, everted configuration.

FIGS. 2A-2G illustrate a method of removing clot material from a blood vessel lumen using the clot retrieval device shown in FIGS. 1A and 1B.

FIG. 3A is a cross-sectional side view of the retrieval device in FIG. 1A being advanced distally through a delivery sheath.

FIGS. 3B-3D are enlarged cross-sectional side views of a proximal portion of the retrieval device in FIG. 3A showing a securing element in a stationary state, a first state, and a second state, respectively.

DETAILED DESCRIPTION

Figure 2A:
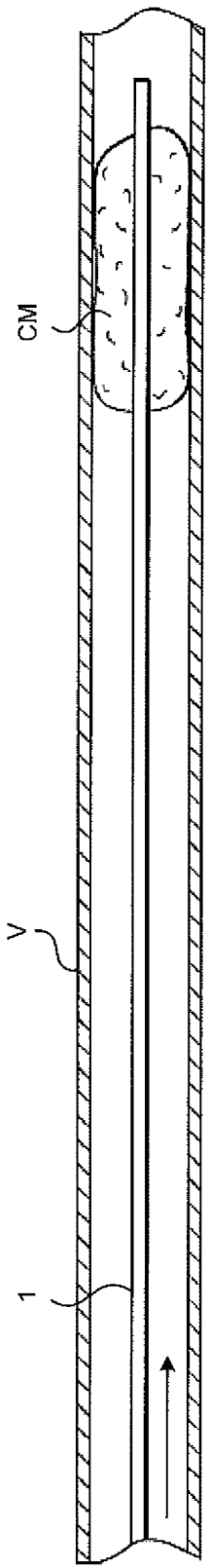

The present technology provides devices, systems, and methods for securing a flexible interventional device against an inner wall of a delivery sheath to assist in resheathing the device while positioning the device in a blood vessel lumen. Although many of the embodiments are described below with respect to devices, systems, and methods for removing clot material from a blood vessel lumen or otherwise treating a cerebral embolism, other applications and other embodiments in addition to those described herein are within the scope of the technology. For example, the securing devices of the present technology may be used to secure any flexible interventional device (e.g., a mesh, a braid, a fabric, etc.) configured to be intravascularly delivered to a body lumen through a delivery sheath.

FIGS. 1A and 1B are side views of a distal portion of some embodiments of a retrieval device 10 ("device 10") outside of a blood vessel in an expanded, relaxed (e.g., unconstrained) configuration in accordance with the present technology. The retrieval device 10 is shown in first and second configurations in FIGS. 1A and 1B, respectively. As shown in FIGS. 1A and 1B, the retrieval device 10 includes an elongated shaft 12 ("shaft 12") and a retrieval assembly 14 coupled to a distal region of the elongated shaft 12 via a connection assembly 120. The retrieval assembly 14 is configured to be intravascularly positioned at or adjacent clot material (or other material to be retrieved such as plaques, foreign bodies, etc.) within a blood vessel lumen and includes a capture structure 100 and a flexible cover 200. In some embodiments, the capture structure 100 and the cover 200 are fixed to the elongated shaft 12 at generally the same location, or the capture structure 100 and cover 200 may be coupled to the shaft 12 at different locations and/or may be slidable with respect to the elongated shaft 12.

The capture structure 100 has a low-profile configuration (not shown) when constrained within a delivery catheter (e.g., a microcatheter) and an expanded configuration for securing and/or engaging clot material or other obstructions within a blood vessel lumen (e.g., a cerebral blood vessel lumen) and/or for restoring blood flow within the blood vessel. The capture structure 100 has a proximal portion 100a coupled to the shaft 12 and a distal portion 100b. The capture structure 100 further includes an open cell framework or body 108 (FIG. 1A) and a coupling region 102 (FIG. 1A) extending proximally from the body 108. In some embodiments, for example as shown in FIGS. 1A and 1B, a distal portion 100b of the capture structure 100 can be generally tubular (e.g., cylindrical), and the proximal portion 100a of the capture structure 100 tapers proximally to the coupling region 102. In some embodiments, the distal terminus of the distal portion 100b coincides with a distal terminus 101 of the capture structure 100 and/or retrieval assembly 14.

Referring again to FIGS. 1A and 1B, in some embodiments the capture structure 100 is a mesh structure formed of a superelastic material (e.g., Nitinol or other resilient or self-expanding material) configured to self-expand when released from the delivery catheter. For example, in some embodiments the capture structure 100 may be a stent and/or stentriever, such as Medtronic's Solitaire™ Revascularization Device, Stryker Neurovascular's Trevo® ProVue™ Stentriever, or other suitable devices. In other embodiments, the capture structure 100 may include a plurality of braided filaments. Examples of suitable capture structures 100 include any of those disclosed in U.S. Pat. No. 7,300,458, filed Nov. 5, 2007, U.S. Pat. No. 8,940,003, filed Nov. 22, 2010, U.S. Pat. No. 9,039,749, filed Oct. 1, 2010, and U.S. Pat. No. 8,066,757, filed Dec. 28, 2010, each of which is incorporated by reference herein in its entirety.

The cover 200 includes a first end portion 200*a* coupled to the shaft 12 via the connection assembly 120, a free second end portion 200*b*, and a cover wall 200*c* extending between the first end portion 200*a* and the second end portion 200*b*. As used herein to describe the second end portion 200*b* of the cover 200, the term "free" refers to a portion of the cover 200 that is not fixed to the elongated shaft 12 and may move radially and/or longitudinally with respect to the shaft 12. The cover 200 is flexible such that it is movable between a first position (FIG. 1A) in which the free second end portion 200*b* is proximal of the first end portion 200*a* and a second position (FIG. 1B) in which the cover 200 is inverted over the capture structure 100 such that a distal terminus 201 (FIG. 1B) of the cover 200 is at or distal to the distal terminus 101 of the capture structure 100 and/or to the first end portion 200*a*. As shown in FIG. 1A, when the cover 200 is in the first position in an expanded, relaxed state, some embodiments of the cover 200 may have a leading edge 204 that overlaps the coupling region 102 of the capture structure 100 but does not extend beyond the coupling region 102 to overlap the body 108 of the capture structure 100. In some embodiments, the leading edge 204 of the cover 200 may also overlap all or a portion of the length of the body 108 when the cover 200 is in the first position. As shown in FIG. 1B, when the cover 200 is in the second position, the free second end portion 200*b* is distal of the first end portion 200*a* and distal of the distal terminus 101 of the capture structure 100. As such, when in the second position, the cover wall 200*c* surrounds the capture structure 100.

The cover 200 can comprise a mesh and/or braid of a plurality of wires (e.g., filaments, threads, sutures, fibers or the like) that have been interwoven to form a structure having openings (e.g., a porous fabric). The mesh and/or braid can be composed of metals, polymers, composites, and/or biologic materials. Polymer materials can include Dacron, polyester, polypropylene, nylon, Teflon, polytetrafluoroethylene (PTFE), tetrafluoroethylene, polyethylene terephthalate, polyactic acid (PLA) silicone, polyurethane, polyethylene, polycarbonate, styrene, polyimide, PEBAX, Hytrel, polyvinyl chloride, high-density polyethylene, low-density polyethylene, polyether ether ketone (PEEK), rubber, latex, and/or other suitable polymers known in the art. Other materials known in the art of elastic implants can also be used. Metal materials can include, but are not limited to, nickel-titanium alloys (e.g. Nitinol), platinum, cobalt-chromium alloys, stainless steel, tungsten or titanium. In certain embodiments, metal filaments may be highly polished and/or surface treated to further improve their hemocompatibility. The cover 200 can be constructed solely from metallic materials without the inclusion of any polymer materials, solely from polymer materials without the inclusion of any metallic materials, or a combination of polymer and metallic materials.

In some embodiments, some or all of the wires of the cover 200 are drawn-filled tube ("DFT") wires having a radiopaque core (e.g., platinum, tantalum, gold, tungsten, etc.) surrounded by a superelastic material (e.g., Nitinol, a cobalt-chromium alloy, etc.). The radiopaque core may comprise about 5% to about 50% (e.g., 10%, 15%, 20%, 25%, 30%, 35%, 40%, 45%) of the total-cross-sectional area of the individual wires. In some embodiments, the cover 200 may have 72-144 total wires (e.g., 72, 96 128, 144, etc.) Moreover, some or all of the wires may have a wire diameter of about 0.005 inches to about 0.015 inches (e.g., 0.008 inches, 0.01 inches, etc.). In some embodiments, all of the wires have the same diameter, and in other embodiments some of the wires have different diameters.

Figure 2B:
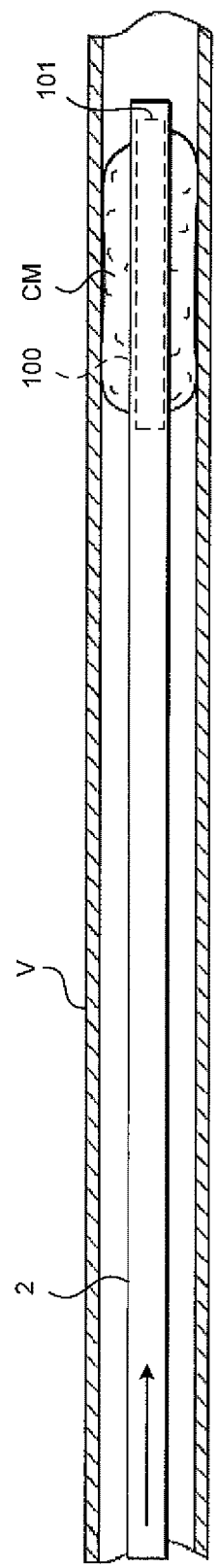
Figure 2C:
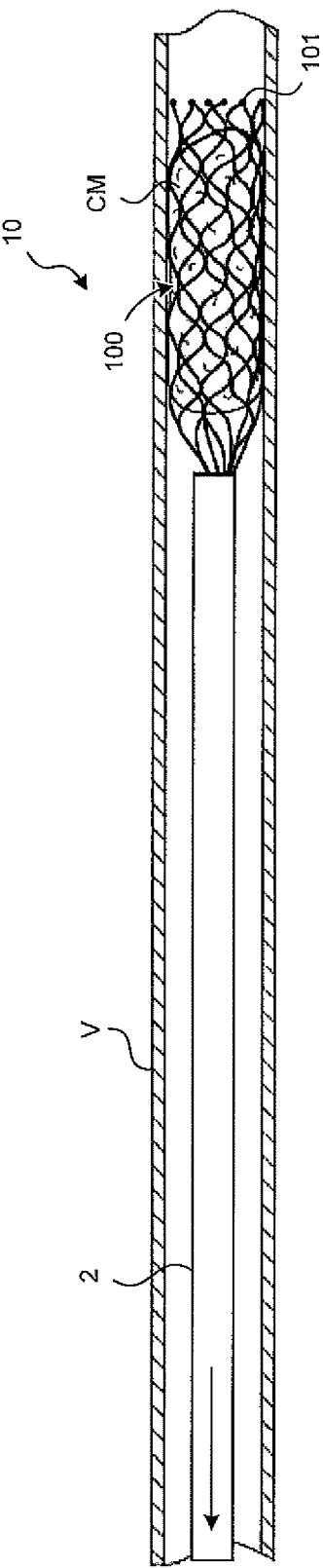
Figure 2D:
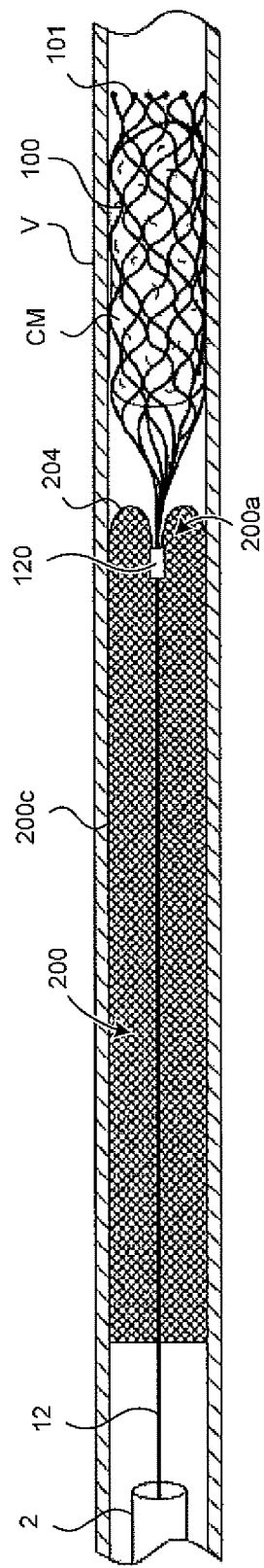

FIGS. 2A-2G illustrate a method of removing clot material from the lumen of a blood vessel V using the retrieval device 10 of the present technology. The retrieval device 10 shown in FIGS. 2A-2G does not include the securing element 330, which is described in detail below with reference to FIGS. 3A-4B. As shown in FIG. 2A, a guidewire 1 may be advanced through the clot material CM such that a distal terminus of the guidewire 1 is distal of the clot material CM. Next, a delivery catheter 2 may be delivered over the guidewire 1 so that a distal portion of the delivery catheter 2 is positioned at or near the clot material CM. As shown in FIG. 2B, in some embodiments the delivery catheter 2 may be advanced over the guidewire 1 through the clot material CM such that a distal terminus of the delivery catheter 2 is distal of the clot material CM. With the delivery catheter 2 in position, the guidewire 1 may be withdrawn. The retrieval device 10 may then be advanced through the delivery catheter 2 in a low-profile configuration until a distal terminus 101 of the capture structure 100 (shown schematically in FIG. 2B) is at or adjacent the distal terminus of the delivery catheter 2. As shown in FIGS. 2C and 2D, the delivery catheter 2 may then be pulled proximally relative to the retrieval device 10 to release the capture structure 100, thereby allowing the capture structure 100 to self-expand within the clot material CM. As the capture structure 100 expands, the capture structure 100 engages and/or secures the surrounding clot material CM, and in some embodiments may restore or improve blood flow through the clot material CM. In some embodiments, the capture structure 100 may be expanded distal of the clot material CM such that no portion of the capture structure 100 is engaging the clot material CM while the capture structure 100 is in the process of expanding toward the vessel wall. In some embodiments, the capture structure 100 is configured to expand into contact with the blood vessel wall, or the capture structure 100 may expand to a diameter that is less than that of the blood vessel lumen such that the capture structure 100 does not engage the entire circumference of the blood vessel wall.

As shown in FIG. 2D, the delivery catheter 2 may continue advancing proximally (as the user continues pulling it proximally) to release the cover 200 such that at least a portion of the cover wall 200*c* expands into contact with the blood vessel wall when the cover 200 is in the first position. Once the delivery catheter 2 is moved proximal of the cover 200 in the first position and both the cover 200 and the capture structure 100 are expanded within the vessel lumen, the retrieval assembly 14 is in the first configuration.

Figure 2E:
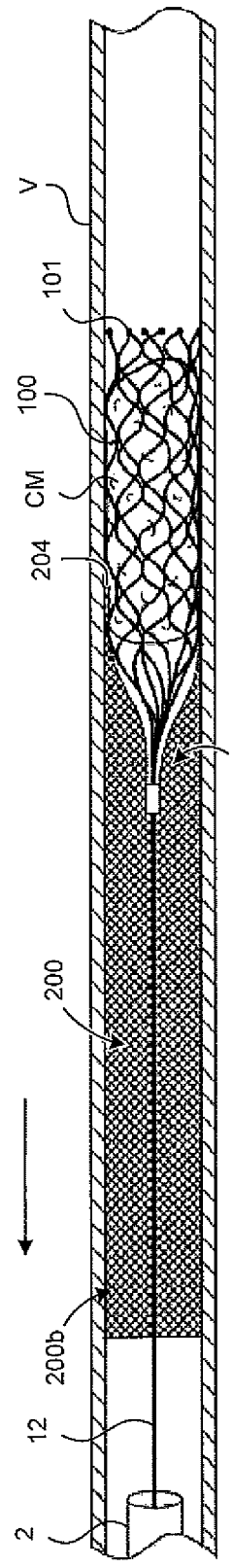
Figure 2F:
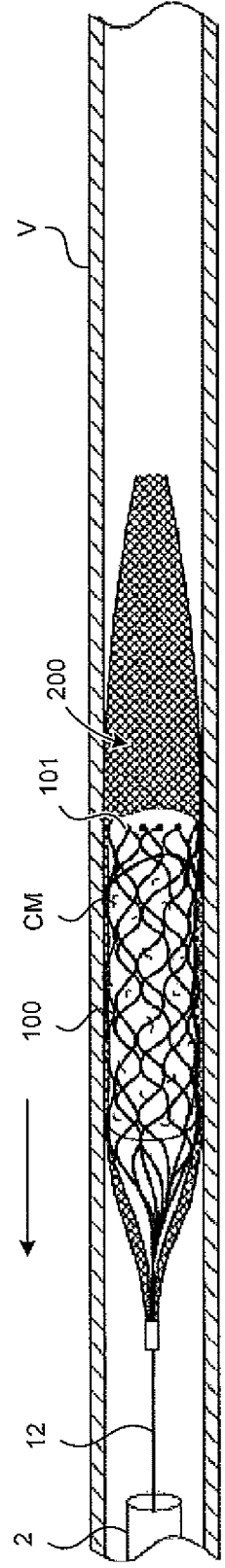

As shown in FIG. 2E, when the elongated shaft 12 is pulled proximally while the retrieval assembly 14 is in the first configuration, friction between the blood vessel wall and the cover wall 200*c* prevents or resists proximal movement of the free second end portion 200*b* of the cover 200 while the first end portion 200*a* of the cover 200 moves in a proximal direction with the capture structure 100. In other words, expansion of the cover 200 provides sufficient friction against the walls of the vessel V to overcome the column strength of the cover wall 200*c*, thereby causing the cover wall 200*c* to remain in place and/or move less than the first end portion 200a of the cover 200 so that the cover wall 200c inverts over the proximally advancing capture structure 100 and any associated clot material CM. As the elongated shaft 12 is moved proximally and the cover 200 is inverting, the capture structure 100 moves proximally relative to the leading edge 204 of the cover 200 so that the length of the capture structure 100 coextensive with the cover 200 increases. Eventually, the cover 200 completely inverts from the first position over the capture structure 100, thereby further securing any clot material held by or within the capture structure. As shown in FIG. 2G, the retrieval device 10 may continue advancing proximally (as the user continues pulling it proximally) until the retrieval assembly 14 is positioned within the delivery catheter 2. The delivery catheter 2, device 10, and associated clot material CM may then be withdrawn from the patient.

In some instances, the physician may desire to move the retrieval assembly 14 proximally relative to the delivery catheter 2 while at least a portion of the retrieval assembly 14 is still within the delivery catheter 2. For example, in some instances it may be desirable to pull at least a portion of the retrieval assembly 14 back into the delivery catheter 2 mid-deployment so that the retrieval assembly 14 can be repositioned and redeployed. More specifically, the physician might advance the capture structure 100 and part of the cover 200 outside of the delivery catheter 2 before determining that the retrieval assembly 14 is not at a desired location within a blood vessel. In other instances, it may be desirable to retract the retrieval assembly 14 proximally when it has yet to be deployed and is still fully within the delivery catheter 2. As used herein, the term "resheath" encompasses any proximal movement of the retrieval assembly 14 within the delivery catheter 2, whether or not the retrieval assembly 14 has been partially deployed from (i.e., advanced outside of) the delivery catheter 2.

While the free second end portion 200b of the cover 200 allows the cover 200 to invert over the capture structure 100, it can hinder efforts to resheath the retrieval assembly 14 within the delivery catheter 2. Specifically, when the retrieval assembly 14 is retracted proximally with no means of securing the cover 200, friction between the delivery catheter 2 and the cover wall 200c can prevent or resist proximal movement of the free second end portion 200b of the cover 200 while the first end portion 200a of the cover 200 moves in a proximal direction with the shaft 12 (e.g., in a similar manner to the intended movement of the cover 200 within a vessel lumen). This can cause the cover 200 to bunch up within the delivery catheter 2 and/or snag on the capture structure 100. As a result, the physician might have to fully remove the retrieval assembly 14 from the delivery catheter 2 (e.g., through a larger outer catheter) in order to prepare the retrieval assembly 14 for redeployment. As described in further detail below with reference to FIGS. 3A-4B, a securing element 330 can be configured to secure the cover 200 while the retrieval assembly 14 is resheathed, thereby making it possible, and/or reducing the time required, to redeploy the retrieval assembly 14.

FIG. 3A is a cross-sectional side view showing the retrieval assembly 14 constrained within a delivery sheath 415. The cover 200 is in the first position (i.e., the free second end portion 200b is proximal of the first end portion 200a) and positioned between the securing element 330 and an interior surface 417 of the delivery sheath 415. The securing element 330 is coupled to the shaft 12 via the first connector 332 and the second connector 334 (collectively "connectors 332, 334"). In some embodiments, the first connector 332 is fixed to the shaft 12 and the second connector 334 is slidably coupled to the shaft 12. Accordingly, when the shaft 12 moves proximally, the shaft 12 can slide proximally by some distance through the second connector 334 such that the first connector 332 moves toward the second connector 334. Likewise, when the shaft 12 moves distally, the shaft 12 can slide distally by some distance through the second connector 334 such that the first connector 332 moves apart from the second connector 334. Changes in the position of the second connector 334 relative to the first connector 332 can correspondingly change characteristics of the securing element 330—such as its shape, cross-sectional dimension (e.g., radius), etc. In some embodiments, the securing element 330 is fixedly coupled to the shaft 12 at the second connector 334 and slidably coupled to the shaft 12 at the first connector 332, or the securing element 330 is fixedly coupled or slidably coupled at both connectors 332, 334.

As shown in FIG. 3A, the securing element 330 can radially expand within the delivery sheath 415 such that the securing element 330 contacts the cover 200 and exerts an outward force against both the cover 200 and the interior surface 417 of the delivery sheath 415. In some embodiments, the securing element 330 is radially biased such that it expands outward and contacts the cover 200 while the shaft 12 is advanced distally, retracted proximally, and held stationary. In some embodiments, the securing element 330 only expands outward and contacts the cover 200 when the elongated shaft 320 is retracted proximally. This may be done, for example, by configuring the first connector 332 as a fixed connector and the second connector 334 as a moveable connector.

The securing element 330 can be a braid or stent, a laser cut expandable component such as a sphere, a compressible foam rubber or polymer pad (in either case in suitable shape such as a cylinder, sleeve or sphere), or one or more struts extending between the first connector 332 and the second connector 334. In one embodiment, the securing element 330 is a heat-set array of nitinol wires. The size of the wires and the shape and configuration of the array can be chosen to give the securing element 330 different characteristics. For example, in some embodiments, using thicker wires or increasing the number of wires in the array can increase a frictional force between the securing element 330 and the cover 200. The securing element 330 can further have any suitable shape or relative size. For example, the securing element 330 can have a generally spherical shape or an outer surface with a different generally curved or angular shape.

Figure 3C:
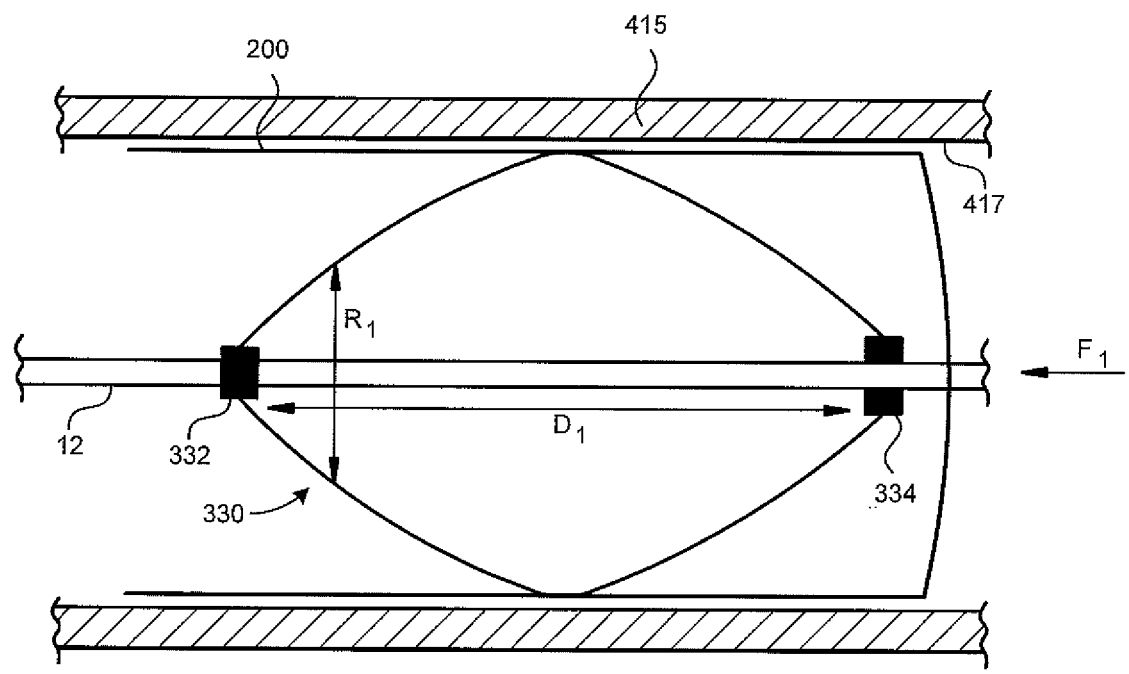
Figure 3D:
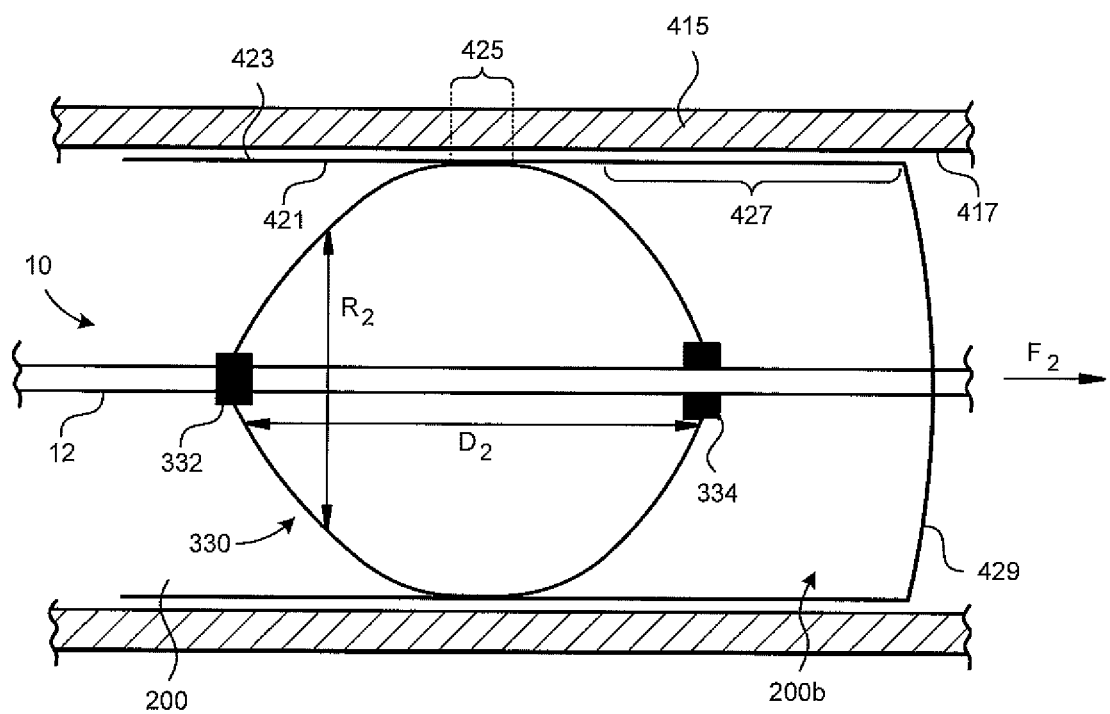

FIGS. 3B-3D are enlarged cross-sectional side views of the securing element 330 in a stationary state, a first state, and a second state, respectively. FIG. 3B shows the securing element 330 in the stationary state in which no force is applied to the shaft 12 (i.e., the shaft 12 is neither being advanced distally nor retracted proximally). As shown, the securing element 330 expands radially outward and contacts the cover 200. In other embodiments, the securing element 330 is configured to not contact the cover 200 in the stationary state. For example, the securing element 330 can be compressed against the shaft 12 or, in an unconstrained state, only expand radially outward to a smaller diameter than the cover 200 in the stationary state within the delivery sheath 415. A distance $D_S$ between the connectors 332, 334 along the shaft 12 depends on the extent of expansion of the securing element 330 and the relative dimensions of the securing element 330 and the delivery sheath 415, among other factors. The securing element 330 can further have a cross-sectional dimension (e.g., area) defined along the plane $R_S$ that depends on the distance $D_S$ and the dimensions of the delivery sheath 415.

FIG. 3C illustrates the securing element 330 in the first state when the shaft 12 is advanced distally in the direction of force $F_1$. Advancing the shaft 12 distally pushes the first connector 332 distally and causes the shaft 12 to slide distally through the second connector 334 such that a distance $D_1$ between the connectors 332, 334 increases relative to when the securing element 330 is in the stationary state (FIG. 3B). As the distance $D_1$ increases, the securing element 330 contracts radially and a cross-sectional dimension (e.g., area) of the securing element 330 defined along the plane $R_1$ correspondingly decreases. The distance $D_1$ depends on the magnitude of the force $F_1$ applied to the shaft 12 in the distal direction, the radial bias of the securing element 330, and the relative dimensions of the securing element 330 and the delivery sheath 415, among other factors. As illustrated in FIG. 3C, the securing element 330 can have an outer surface that has a generally angular shape in the first state.

In the embodiment shown in FIG. 3C, the securing element 330 can exert a moderate outward force against the cover 200 and an interior surface 417 of the delivery sheath 415 in the first state. The outward force exerted against the cover 200 in the first state is not enough to hinder distal advancement of retrieval assembly 14. That is, the retrieval assembly 14 can be advanced through the delivery sheath 415 despite the friction between the cover 200 and the interior surface 417 of the delivery sheath 415 caused by the securing element 330 in the first state. In other embodiments, the securing element 330 is configured not to exert an outward force against the cover 200 while the shaft 12 is advanced distally. For example, the securing element 330 can compress down to the shaft 12 such that it does not contact the cover 200 in the first state.

FIG. 3D illustrates the securing element 330 in the second state when the shaft 12 is retracted proximally in the direction of force $F_2$. Proximal movement of the shaft 12 pulls the first connector 332 proximally and causes the shaft 12 to slide proximally through the second connector 334 such that a distance $D_2$ between the connectors 332, 334 along the shaft 12 is less than the distance $D_1$ in the first state (FIG. 3C) and the distance $D_S$ in the stationary state (FIG. 3B). As the securing element 330 foreshortens (i.e., the distance $D_2$ decreases), the securing element 330 expands radially outward such that a cross-sectional dimension (e.g., diameter) of the securing element 330 defined along the plane $R_2$ correspondingly increases. The distance $D_2$ depends on the magnitude of the force $F_2$ applied to the shaft 12 in the proximal direction, the radial bias of the securing element 330, and the relative dimensions of the securing element 330 and the delivery sheath 415, among other factors.

In the second state, the securing element 330 contacts and pushes outwardly against the cover 200 at a contact region 425 of the cover 200. The contact region 425 can have a greater or smaller area depending on the configuration of the securing element 330 and the amount of force $F_2$ applied to the shaft 12. For example, in some embodiments, as the distance $D_2$ between the connectors 332, 334 decreases (e.g., the Force $F_2$ is increased), the contact region 425 becomes larger as the securing element 330 expands radially. The securing element 330 exerts a force against the cover 200 at the contact region 425, and indirectly exerts a force against the interior surface 417 of the delivery sheath 415 (i.e., through the cover 200). The force exerted by the securing element 330 on the cover 200 can be greater in the second state than in the stationary state (FIG. 3B) and the first state (FIG. 3C).

In operation, the securing element 330 secures (e.g., grips) the cover 200 in the second state. For example, the securing element 330 is configured such that there is more friction between the securing element 330 and an inner surface 421 of the cover 200 than between an outer surface 423 of the cover 200 and the interior surface 417 of the delivery sheath 415 in the second state. More specifically, friction between the securing element 330 and the contact region 425 of the cover 200 causes a frictional force that opposes relative motion between the securing element 330 and the cover 200. Therefore, the cover 200 can slide proximally relative to the delivery sheath 415—but not relative to the securing element 330—when the force $F_2$ is applied to the shaft 12.

The forces acting on the cover 200 can be more complicated than presently described. For example, the physical structure of the cover 200 can introduce a column force when the retrieval assembly 14 is retracted proximally. Moreover, the securing element 330 can impart some horizontal forces on the cover 200 at boundary regions between the contact region 425 and non-contacted portions of the cover 200.

In the embodiment illustrated in FIG. 3D, the contact region 425 is nearer to the free second end portion 200b of the cover 200 than the first end portion 200a of the cover 200. In certain embodiments, a proximal region 427 of the cover 200 is proximal of the contact region 425. In operation, the proximal region 427 is not secured by the securing element 330 as described above. That is, friction between the proximal region 427 and the delivery sheath 415 can prevent or resist proximal movement of the proximal region 427 of the cover 200 (which the securing element 330 is configured to overcome for the rest of the cover 200). This can result in some bunching of the proximal region 427 of the cover 200 when the retrieval assembly 14 is retracted proximally. However, by configuring the proximal region 427 to be small compared to the overall size of the cover 200, the effect can be made to be insubstantial. Accordingly, the retrieval assembly 14 can still be resheathed within the delivery sheath 415 without requiring the physician to fully remove the retrieval assembly 14 to ready it for redeployment.

In some embodiments, the cover 200 does not include any proximal region 427 when the securing element 330 is in the second state. For example, the securing element 330 can be positioned such that the contact region 425 is at or immediately adjacent to a terminus 429 (i.e., absolute end) of the cover 200. In particular, the second connector 334 can be coupled to the shaft 12 at a position that is proximal of the terminus 429 of the cover 200. Accordingly, the terminus 429 can be between the connectors 332, 334 such that, in the second state, the contact region 425 of the cover 200 includes the terminus 429 of the cover 200. In such embodiments, even minor bunching or other undesired movement of the cover 200 can be avoided as the retrieval assembly 14 is retracted proximally.

In order for the securing element 330 to secure the cover 200 as described above, at least a portion of the cover 200 and a portion of the securing element 330 must remain within the delivery sheath 415. In particular, at least portion of the contact region 425 of the cover 200 must be within the delivery sheath 415 to enable resheathing of the retrieval assembly 14. In some embodiments, the securing element 330 is configured to expand outward against the cover 200 when the securing element 330 is fully outside of the delivery sheath 415 and within a vessel lumen. In some such embodiments, the securing element 330 helps expand the cover 200 within the vessel lumen to facilitate moving the cover 200 to the second position (FIG. 1B).

Figure 4A:
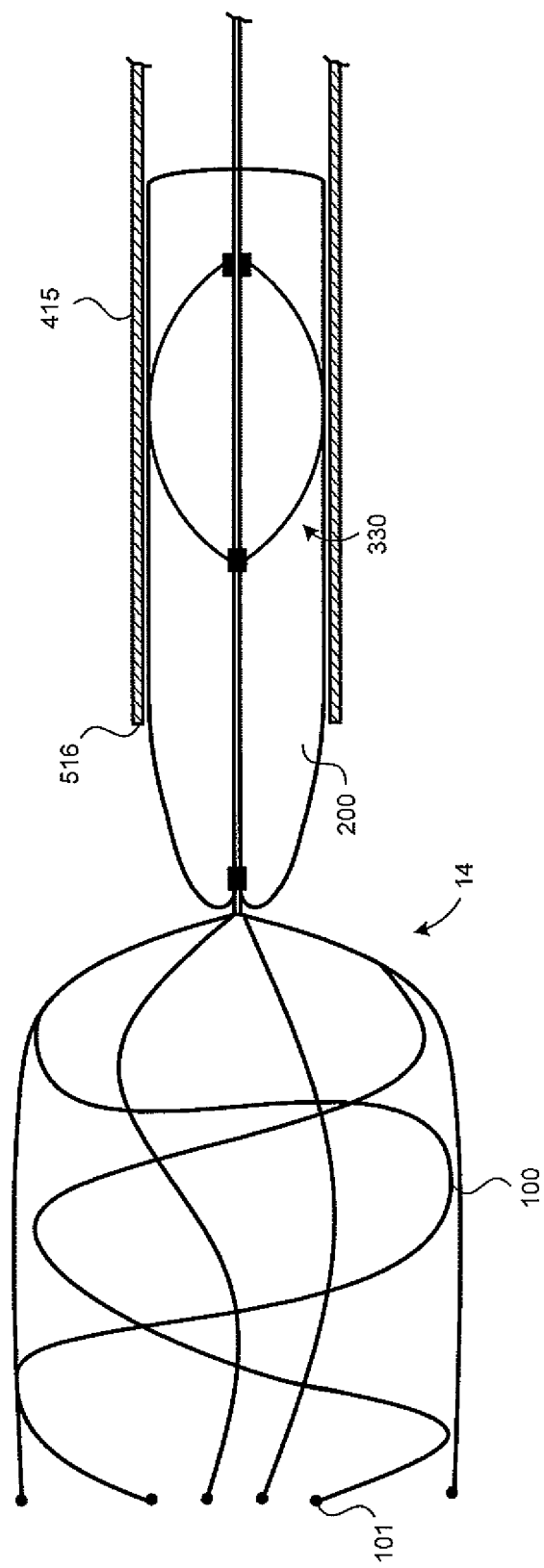
FIG. 4A is a cross-sectional side view of the retrieval device in FIG. 1A, being held stationary, and in a partially deployed position from a delivery sheath.
Figure 4B:
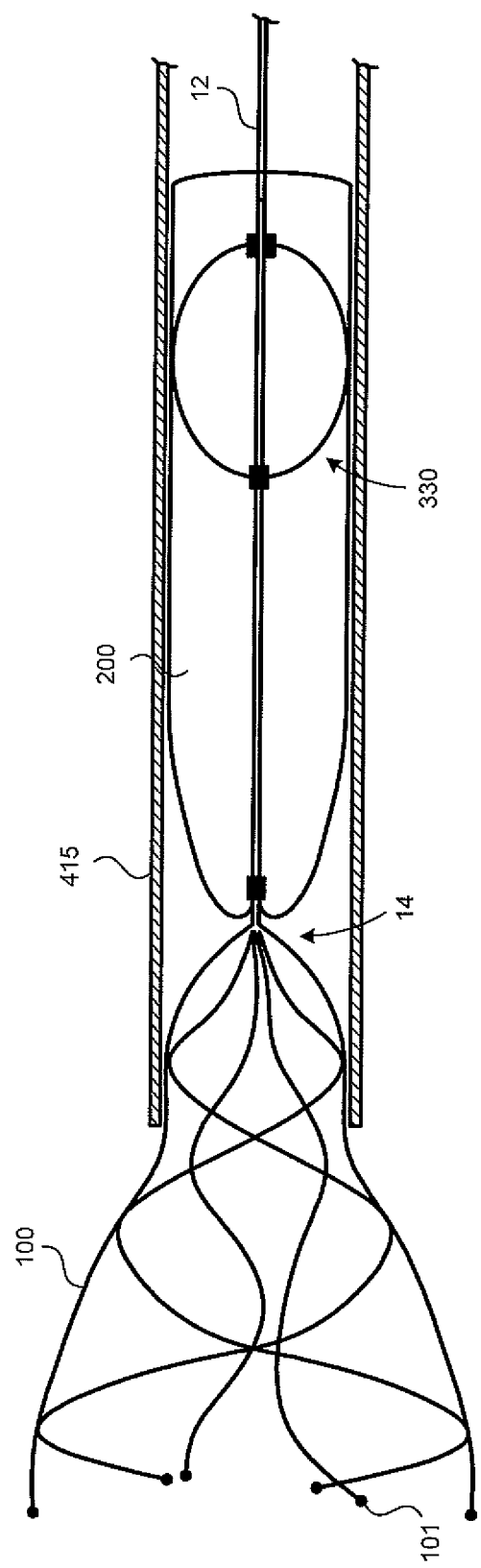
FIG. 4B is a cross-sectional side view of the retrieval device in FIG. 1A, being retracted proximally, and in a partially deployed position from the delivery sheath.

FIGS. 4A and 4B illustrate various stages of a method for resheathing the retrieval assembly 14 including the securing element 330 in accordance with embodiments of the present technology. In operation, the delivery sheath 415 with the retrieval assembly 14 positioned therein (as shown in FIG. 3A) can be positioned at a treatment site. As shown in FIG. 4A, the retrieval assembly 14 can then be advanced to a partially deployed position. In the partially deployed position: (i) at least a portion of the cover 200 remains within the delivery sheath 415, and (ii) at least a portion of the securing element 330 remains within the delivery sheath 415. In some embodiments, at least the distal terminus 101 of the capture structure 100 is distal of the of the delivery sheath 415 (e.g., extends past a distal terminus 516 of the delivery sheath 415) in the partially deployed position. As shown in FIG. 4B, the capture structure 100 is fully outside of the delivery sheath 415, a portion of the cover 200 is within the delivery sheath 415, and the securing element 330 is fully within the delivery sheath 415.

FIG. 4A shows the securing element 330 in the stationary state. As the retrieval assembly 14 is advanced to the partially deployed position shown in FIG. 4A, the securing element 330 can be in the first state. However, before fully deploying the retrieval assembly 14, the physician first assesses whether the retrieval assembly 14 is located at a desired location within the vasculature (e.g., at the site of clot material to be removed). When distal advancement is stopped, the securing element 330 can be in the stationary state as illustrated in FIG. 4A. If the physician determines that the retrieval assembly 14 is in the desired location, the physician can then advance the retrieval assembly 14 to a deployed state (e.g., where the cover 200 and capture structure 100 are fully outside the delivery sheath 415). However, if the physician determines that the there is a more desirable location, the physician can resheath the retrieval assembly 14 within the delivery sheath 415 so that the retrieval assembly 14 can be moved to, and later deployed at, another location.

FIG. 4B shows the retrieval assembly 14 in another partially deployed state and being retracted (to the right of the page) to a position more proximal within the delivery sheath 415. In the partially deployed state shown in FIG. 4B: (i) the distal terminus 101 of the capture structure 100 is outside the delivery sheath 415, (ii) a portion of the capture structure 100 is within the delivery sheath 415, and (iii) the cover 200 is fully within the delivery sheath 415. A physician may retract the retrieval assembly 14 by pulling proximally on the shaft 12, or by otherwise applying a proximal force to the shaft 12. During retraction, the securing element 330 grips the cover 200 in the second state to prevent substantial movement of the cover 200 relative to the shaft 12. Therefore, the retrieval assembly 14 can be resheathed without significant bunching of the cover 200 that would otherwise impede the resheathing process. In some embodiments, the retrieval assembly 14 is retracted proximally until it is fully within the delivery sheath 415 (as shown in FIG. 3A). In other embodiments, only a portion of the retrieval assembly 14 is retracted to a more proximal position within the delivery sheath 415 (e.g., from the partially deployed position shown in FIG. 4A to the partially deployed position shown in FIG. 4B).

Once resheathed, the delivery sheath 415 can be moved to reposition the retrieval assembly 14 at another location within the vasculature. Some embodiments of the present technology accordingly can allow the physician to partially deploy and then resheath the retrieval assembly 14 as many times as necessary.

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown and/or described in detail to avoid unnecessarily obscuring the description of the embodiments of the present technology. Although steps of methods may be presented herein in a particular order, in alternative embodiments the steps may have another suitable order. Similarly, certain aspects of the present technology disclosed in the context of particular embodiments can be combined or eliminated in other embodiments. Furthermore, while advantages associated with certain embodiments may have been disclosed in the context of those embodiments, other embodiments can also exhibit such advantages, and not all embodiments need necessarily exhibit such advantages or other advantages disclosed herein to fall within the scope of the present technology. Accordingly, this disclosure and associated technology can encompass other embodiments not expressly shown and/or described herein.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like are used throughout this disclosure to mean including at least the recited feature(s) such that any greater number of the same feature(s) and/or one or more additional types of features are not precluded. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

We claim:

1. A retrieval device deployable through a delivery sheath, the device comprising:
    an elongated shaft;
    a retrieval structure coupled to a distal zone of the elongated shaft, the retrieval structure including a capture structure and a cover having (a) a first portion coupled to the distal zone of the elongated shaft at a location proximal of the capture structure and (b) a free second portion, wherein, in a delivery state, the second portion of the cover extends proximally from the first portion; and
    a securing element coupled to the elongated shaft proximal to the first portion of the cover,
    wherein, when the cover is in the delivery state and at least a portion of the cover and at least a portion of the securing element are positioned within the delivery sheath, moving the retrieval device proximally increases an outward force exerted by the securing element against at least a portion of the cover and an inner surface of the delivery sheath, thereby inhibiting movement of the second portion of the cover relative to the elongated shaft.

2. The retrieval device of claim 1 wherein the cover extends continuously between the first portion and the second portion, and wherein the securing element exerts the outward force against the cover nearer to the second portion than the first portion.

3. The retrieval device of claim 1 wherein:
the securing element is in a first state when positioned at least partially within the delivery sheath and the retrieval device is moved proximally with respect to the delivery sheath,
the securing element is in a second state when positioned at least partially within the delivery sheath and the retrieval device is moved distally with respect to the delivery sheath, and
the securing element exerts an outward force against the cover that is less in the second state than in the first state.

4. The retrieval device of claim 1 wherein:
the securing element is in a first state when positioned at least partially within the delivery sheath and the retrieval device is moved proximally with respect to the delivery sheath,
the securing element is in a second state when positioned at least partially within the delivery sheath and the retrieval device is moved distally with respect to the delivery sheath, and
the securing element has a cross-sectional area that is greater in the first state than in the second state.

5. The retrieval device of claim 1 wherein the securing element is a braid or stent coupled to the elongated shaft at a first connector and a second connector, and wherein the first connector is proximal to the second connector along the shaft.

6. The retrieval device of claim 5 wherein at least one of the first and second connectors is fixed to the elongated shaft.

7. The retrieval device of claim 5 wherein at least one of the first and second connectors is slidably coupled to the elongated shaft and the other of the first and second connectors is fixed to the elongated shaft.

8. The retrieval device of claim 5 wherein the securing element includes a plurality of struts extending from the first connector to the second connector.

9. The retrieval device of claim 1 wherein the securing element is at least one of a laser cut sphere, a compressible foam or polymer pad, and a braided structure.

10. The retrieval device of claim 1 wherein at least one of the capture structure and the cover is a mesh.

11. The retrieval device of claim 1 wherein the capture structure is a stent and the cover is a braid.

12. The retrieval device of claim 1 wherein, when the retrieval structure is in the delivery state and the securing element is outside of the delivery sheath and within a vessel lumen, the securing element is configured to expand outward against the cover within the vessel lumen.

13. The retrieval device of claim 1 wherein the securing element is an expandable component.

14. The retrieval device of claim 13 wherein the expandable component is a laser cut component.

15. The retrieval device of claim 13 wherein the expandable component is a sphere.

16. The retrieval device of claim 1 wherein the securing element is a braid.

17. The retrieval device of claim 1 wherein the securing element is a stent.

18. The retrieval device of claim 1 wherein the securing element is a compressible foam rubber.

19. The retrieval device of claim 18 wherein a shape of the compressible foam rubber is a cylinder, sleeve, or sphere.

20. The retrieval device of claim 1 wherein the securing element is a pad.

21. The retrieval device of claim 20 wherein the pad is a polymer pad.

22. The retrieval device of claim 20 wherein a shape of the pad is a cylinder, a sleeve, or a sphere.

23. The retrieval device of claim 1 wherein the securing element is a heat-set array of wires.

24. The retrieval device of claim 1 wherein the securing element has a generally spherical shape.

25. The retrieval device of claim 1 wherein the securing element has an outer surface with a generally curved shape.

26. The retrieval device of claim 1 wherein the securing element has an outer surface with an angular shape.

27. A system for retrieving vascular material, the system comprising:
a delivery sheath having a distal portion;
a retrieval device including an elongated shaft, a retrieval structure, and a securing element, wherein:
the retrieval structure is coupled to a distal zone of the elongated shaft and includes a capture structure and a cover,
the cover has a first portion coupled to the distal zone of the elongated shaft and a free second portion,
in a partially deployed state, at least a distal portion of the capture structure extends past the distal portion of the delivery sheath, at least the second portion of the cover is within the delivery sheath, and the second portion of the cover extends proximally from the first portion, and
the securing element is coupled to the elongated shaft proximal to the first portion of the cover, and the securing element is configured to expand when the device is retracted proximally from the partially deployed state such that the securing element grips at least a portion of the cover between the securing element and an inner surface of the delivery sheath, thereby preventing substantial movement of the second portion of the cover relative to the first portion of the cover while the retrieval device is retracted proximally.

28. The system of claim 27 wherein the capture structure is a stent and the cover is a braid.

29. The system of claim 27 wherein the securing element is coupled to the elongated shaft at a first connector and a second connector, wherein the first connector is proximal to the second connector along the shaft, and wherein the first connector is slidably coupled to the elongated shaft.

30. The system of claim 27 wherein the cover extends continuously between the first portion and the second portion, and wherein the securing element grips the cover nearer to the second portion than the first portion.

31. The system of claim 27 wherein the securing element is an expandable component.

32. The system of claim 31 wherein the expandable component is a laser cut component.

33. The system of claim 31 wherein the expandable component is a sphere.

34. The system of claim 27 wherein the securing element is a braid.

35. The system of claim 27 wherein the securing element is a stent.

36. The system of claim 27 wherein the securing element is a compressible foam rubber.

37. The system of claim 36 wherein a shape of the compressible foam rubber is a cylinder, a sleeve, or a sphere.

38. The system of claim 27 wherein the securing element is a pad.

39. The system of claim 38 wherein the pad is a polymer pad.

40. The system of claim 38 wherein a shape of the pad is a cylinder, sleeve, or sphere.

41. The system of claim 27 wherein the securing element is a heat-set array of wires.

42. The system of claim 27 wherein the securing element has a generally spherical shape.

43. The system of claim 27 wherein the securing element has an outer surface with a generally curved shape.

44. The system of claim 27 wherein the securing element has an outer surface with an angular shape.

\* \* \* \* \*